US008137322B2

(12) United States Patent
Soltz et al.

(10) Patent No.: US 8,137,322 B2
(45) Date of Patent: Mar. 20, 2012

(54) STABILIZATION ASSIST DEVICE FOR TROCAR

(75) Inventors: Michael A. Soltz, North Haven, CT (US); Megan L. Prommersberger, Wallingford, CT (US); Richard D. Gresham, Guilford, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 1274 days.

(21) Appl. No.: 11/880,499

(22) Filed: Jul. 23, 2007

(65) Prior Publication Data
US 2008/0058728 A1    Mar. 6, 2008

(51) Int. Cl.
*A61M 5/32* (2006.01)
(52) U.S. Cl. .................................... 604/174
(58) Field of Classification Search ................ 604/174, 604/175, 176, 164.01–164.11, 913; 606/108
See application file for complete search history.

(56) References Cited

U.S. PATENT DOCUMENTS

| | | |
|---|---|---|
| 1,870,942 A | 8/1932 | Beatty |
| 2,854,983 A | 10/1958 | Baskin |
| 3,108,595 A | 10/1963 | Overment |
| 3,312,215 A | 4/1967 | Silber |
| 3,397,699 A | 8/1968 | Kohl |
| 3,716,051 A | 2/1973 | Fischer |
| 3,779,239 A | 12/1973 | Fischer et al. |
| 3,915,171 A | 10/1975 | Shermeta |
| 3,961,632 A | 6/1976 | Moossun |
| 4,224,929 A | 9/1980 | Furihata |
| 4,409,974 A | 10/1983 | Freedland |
| 4,430,076 A | 2/1984 | Harris |
| 4,453,539 A | 6/1984 | Raftopoulos et al. |
| 4,496,345 A | 1/1985 | Hasson |
| 4,503,843 A | 3/1985 | Boebel |
| 4,608,965 A | 9/1986 | Anspach, Jr. et al. |
| 4,617,933 A | 10/1986 | Hasson |
| 4,641,634 A | 2/1987 | Storz |
| 4,664,114 A | 5/1987 | Ghodsian |
| 4,676,782 A * | 6/1987 | Yamamoto et al. ........... 604/175 |
| 4,716,893 A | 1/1988 | Fischer et al. |
| 4,721,103 A | 1/1988 | Freedland |
| 4,779,612 A | 10/1988 | Kishi |
| 4,820,270 A | 4/1989 | Hardcastle et al. |

(Continued)

FOREIGN PATENT DOCUMENTS

DE    2 411 226    9/1974

(Continued)

OTHER PUBLICATIONS

European Search Report for corresponding EP 09172125 date of mailing is Nov. 16, 2009 (3 pages).

(Continued)

*Primary Examiner* — Jackie Ho
*Assistant Examiner* — Laura Schell

(57) ABSTRACT

A stabilizer is provided to secure and fix the position of a cannula assembly relative to tissue. The stabilizer is a liquid swellable member which expands within an incision in tissue in response to the absorption of a liquid. The stabilizer includes an inner adhesive layer to secure the stabilizer relative to a cannula assembly. The stabilizer is formed of a polymeric gel or foam. In one embodiment, the stabilizer is fixedly secured to an elongate tubular member of a cannula assembly. In an alternative embodiment, the stabilizer is mounted for longitudinal movement along an elongate tubular member of a cannula assembly.

1 Claim, 5 Drawing Sheets

U.S. PATENT DOCUMENTS

| | | |
|---|---|---|
| 4,836,189 A | 6/1989 | Allred, III et al. |
| 4,885,003 A | 12/1989 | Hillstead |
| 4,911,148 A | 3/1990 | Sosnowski et al. |
| 4,921,478 A | 5/1990 | Solano et al. |
| 4,949,718 A | 8/1990 | Neuwirth et al. |
| 4,984,564 A | 1/1991 | Yuen |
| 5,002,557 A | 3/1991 | Hasson |
| 5,041,093 A | 8/1991 | Chu |
| 5,053,009 A | 10/1991 | Herzberg |
| 5,104,377 A | 4/1992 | Levine |
| 5,122,122 A | 6/1992 | Allgood |
| 5,176,697 A | 1/1993 | Hasson et al. |
| 5,188,602 A | 2/1993 | Nichols |
| 5,209,754 A | 5/1993 | Ahluwalia |
| 5,242,390 A | 9/1993 | Goldrath |
| 5,259,836 A | 11/1993 | Thurmond et al. |
| 5,267,970 A | 12/1993 | Chin et al. |
| 5,344,439 A | 9/1994 | Otten |
| 5,352,207 A * | 10/1994 | Nussbaum ............. 604/175 |
| 5,421,832 A | 6/1995 | Lefebvre |
| 5,454,790 A | 10/1995 | Dubrul |
| 5,540,658 A | 7/1996 | Evans et al. |
| 5,613,950 A | 3/1997 | Yoon |
| 5,695,517 A | 12/1997 | Marin et al. |
| 5,792,155 A | 8/1998 | VanCleef |
| 5,803,901 A | 9/1998 | Chin et al. |
| 5,836,913 A | 11/1998 | Orth et al. |
| 5,836,953 A | 11/1998 | Yoon |
| 5,842,971 A * | 12/1998 | Yoon ............................ 600/101 |
| 5,882,345 A | 3/1999 | Yoon |
| 5,891,094 A | 4/1999 | Masterson et al. |
| 5,944,730 A | 8/1999 | Nobles et al. |
| 6,066,132 A | 5/2000 | Chen et al. |
| 6,146,400 A | 11/2000 | Hahnen |
| 6,146,401 A | 11/2000 | Yoon et al. |
| 6,171,319 B1 | 1/2001 | Nobles et al. |
| 6,174,317 B1 | 1/2001 | Engman |
| 6,228,068 B1 | 5/2001 | Yoon |
| 6,231,588 B1 | 5/2001 | Zadno-Azizi |
| 6,312,407 B1 | 11/2001 | Zadno-Azizi et al. |
| 6,355,028 B2 | 3/2002 | Castaneda et al. |
| 6,409,739 B1 | 6/2002 | Nobles et al. |
| 6,464,690 B1 | 10/2002 | Castaneda et al. |
| 6,464,691 B1 | 10/2002 | Castaneda et al. |
| 6,482,178 B1 | 11/2002 | Andrews et al. |
| 6,494,893 B2 | 12/2002 | Dubrul et al. |
| 6,500,113 B2 | 12/2002 | Vilos |
| 6,503,245 B2 | 1/2003 | Palmer et al. |
| 6,511,469 B2 | 1/2003 | Ackerman et al. |
| 6,551,303 B1 | 4/2003 | Van Tassel et al. |
| 6,558,401 B1 | 5/2003 | Azizi |
| 6,582,420 B2 | 6/2003 | Castaneda et al. |
| 6,589,208 B2 | 7/2003 | Ewers et al. |
| 6,592,573 B2 | 7/2003 | Castaneda et al. |
| 6,648,906 B2 | 11/2003 | Lasheras et al. |
| 6,652,555 B1 | 11/2003 | VanTassel et al. |
| 6,652,556 B1 | 11/2003 | VanTassel et al. |
| 6,689,150 B1 | 2/2004 | VanTassel et al. |
| 6,692,462 B2 | 2/2004 | Mackenzie et al. |
| 6,749,574 B2 * | 6/2004 | O'Keefe ..................... 600/561 |
| 2006/0079918 A1 | 4/2006 | Creston |

FOREIGN PATENT DOCUMENTS

| | | |
|---|---|---|
| WO | WO 99/15068 A | 4/1999 |
| WO | WO 02/096307 | 12/2002 |

OTHER PUBLICATIONS

European Search Report for corresponding EP 07252999 date of mailing is Jul. 18, 2008 (3 pages).

* cited by examiner

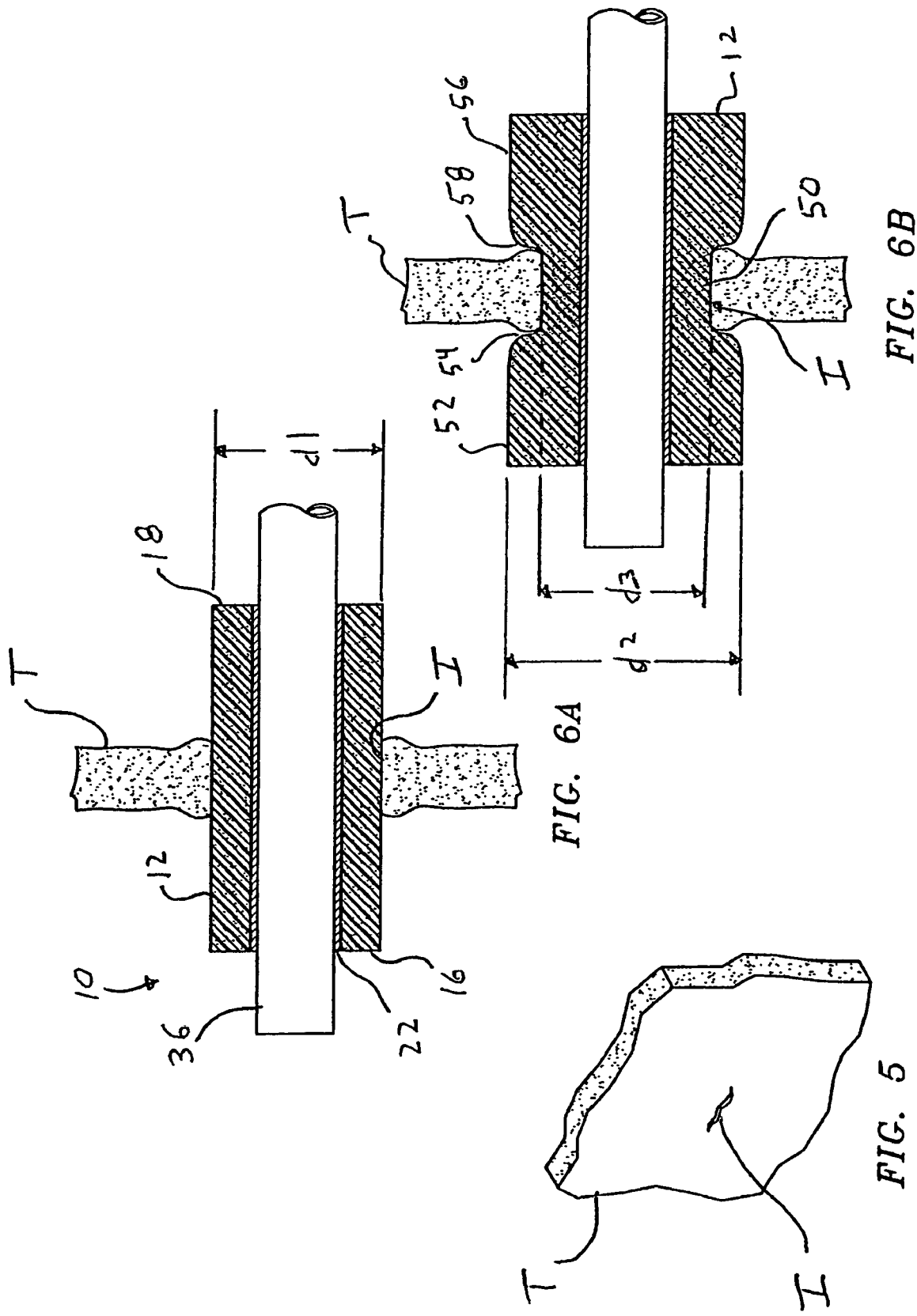

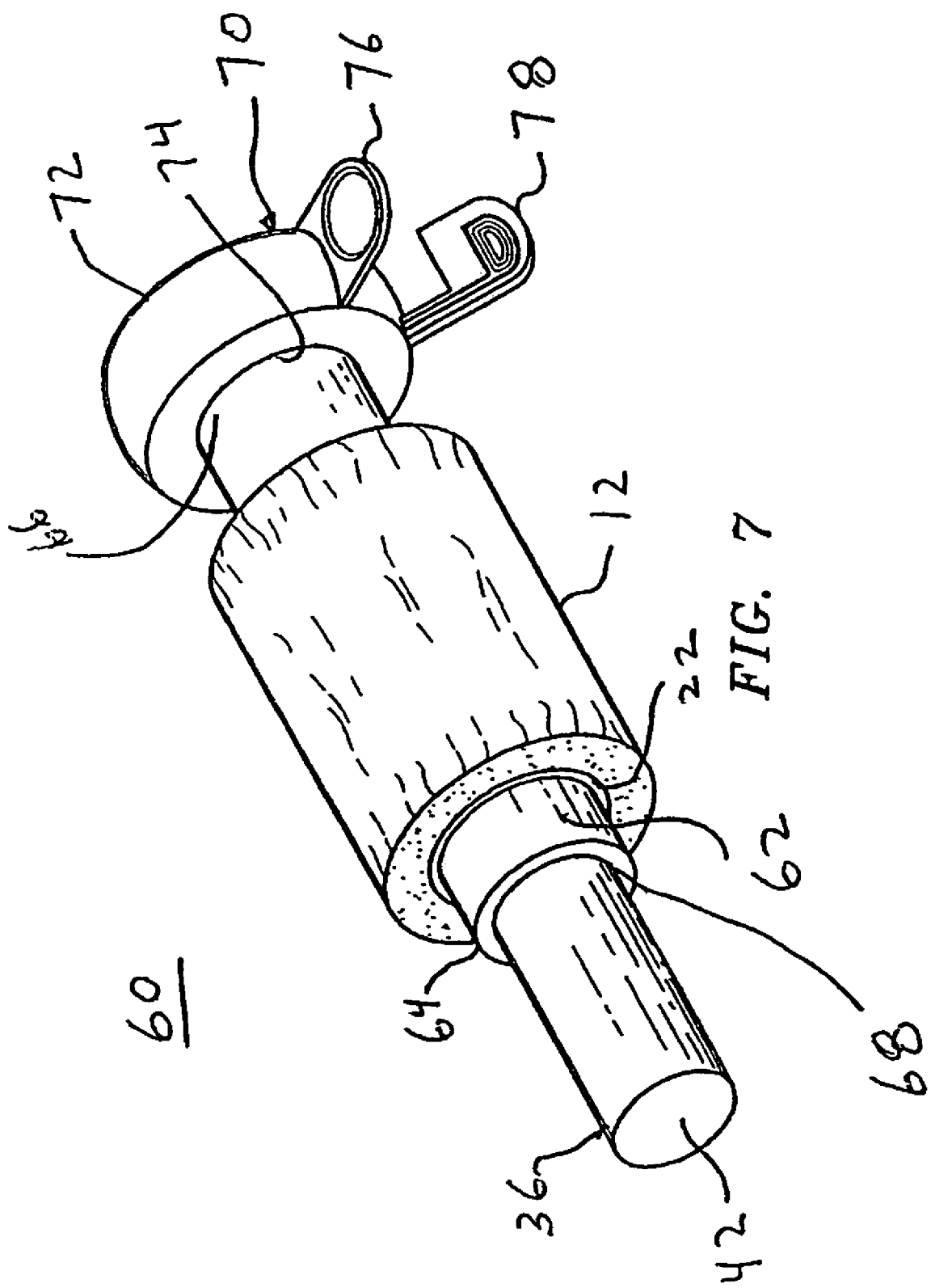

STABILIZATION ASSIST DEVICE FOR TROCAR

BACKGROUND

1. Technical Field

The present disclosure relates to a stabilization assist device. More particularly, the present disclosure relates to a stabilization assist device for use with a trocar cannula or "cannula" to secure and stabilize the cannula's position through an incision.

2. Background of Related Art

Many modern surgical procedures can be performed in a noninvasive manner. Examples of such procedures can include endoscopic and/or laparoscopic surgeries. In these surgeries, a small incision is made through the skin of a patient and an access port or "cannula" is inserted through the incision to provide access to the internal body cavity. For example, a hernia repair surgery may be performed laparoscopically by first forming an incision through the abdominal wall of a patient and inserting the access port or cannula through the incision. Thereafter, surgical instruments may be inserted through the cannula to perform the hernia repair surgery.

When the cannula is inserted through the incision, it is often desirable to secure or stabilize the cannula's position relative to the abdominal wall. Various devices may be provided on the outer surface of the cannula to facilitate stabilization within the abdominal wall, such as, for example, balloons, disks, etc. A particularly suitable method of stabilizing the cannula relative to the abdominal wall includes providing an inflatable balloon at a distal end of the cannula and a securing member slidably mounted on the cannula tube. The cannula is inserted into the incision in the abdominal wall and the balloon inflated to secure the cannula against the inner surface of the abdominal wall. Thereafter, the securing member is advanced against the outer surface of the abdominal wall or a skin and locked in place to fix the depth of the cannula relative to the abdominal wall. And exemplary example of this type of device is disclosed in U.S. patent application Ser. No. 11/235,492, entitled Balloon Anchored Surgical Apparatus, Its Method and Manufacture, filed on Sep. 26, 2005. This particular device includes an open cell foam collar slidably mounted about a cannula tube which is compressible against the outer surface of the skin and cooperates with an inflatable balloon on an inner surface of the skin to secure the cannula relative to the abdominal wall. As it is compressed, the open cell foam collar displaces gas between the cells. When the collar is moved away from the skin air reenters the open cell foam structure and the collar expands to its original shape.

While this device provides an excellent means of securing a cannula to an abdominal wall of a patient it is desirable to provide expandable or swellable cannula stabilization device which can secure a cannula in position relative to the abdominal wall by absorption of bodily, or externally supplied, fluids into the stabilization device. It would be further desirable to provide a stabilization device where the expansion of the device may be reversed by the withdrawal or displacement of fluids from the device. Further, it would be desirable to provide a stabilization device which can seal against the inner surfaces of the incision of the abdominal wall to fully fill the incision with the stabilization device and thus minimize any chance of escape of insufflation fluid or gases from within the body cavity. Additionally, it would be desirable to provide such a stabilization device which is longitudinally movable along the outer surface of the tube of the cannula to adjust the depth of the cannula through the abdominal wall.

SUMMARY

There is disclosed a stabilizer for use in securing a cannula assembly relative to an incision in tissue. A stabilizer generally includes a stabilizing member positionable upon an elongate tubular member of an associated cannula assembly. The stabilizing member is swellable from an initial radial dimension to a greater final radial dimension in response to the absorption of a liquid. The stabilizing member may be formed of an absorbent polymeric gel or foam.

In one embodiment, the stabilizing member is a hollow elongate tubular member which is swellable from an initial radial diameter to a greater final radial diameter in response to the absorption of a liquid. The diameter of the stabilizing member may be reducible from the final diameter back to the initial diameter upon the application of a subsequent material displacing or reabsorbing the liquid from the stabilizing member. The stabilizing member may include a longitudinal slit to facilitate positioning the stabilizing member about the elongate tubular member of the associated cannula assembly.

In one embodiment, the stabilizing member includes an adhesive layer formed on an inner surface of the stabilizing member to secure the stabilizing member to the elongate tubular member of the cannula assembly.

There is also disclosed an adjustable stabilizer for securing a cannula assembly relative to an incision in tissue. The adjustable stabilizer generally includes a hollow tubular member for receipt of a portion of a cannula assembly and a stabilizing member secured to the hollow tubular member and being swellable from an initial radial dimension to a greater final radial dimension in response to the absorption of a liquid. The stabilizing member may also include an inner adhesive layer on an inner surface thereof to secure the stabilizing member to the hollow tubular member.

In one embodiment, the hollow tubular member includes a locking member for securing the hollow tubular member at a predetermined position along the length of a cannula assembly. The locking member is a spring biased clamp. The spring biased clamp is positioned at a proximal end of the hollow tubular member and proximally of the stabilizing member. The stabilizing member may be formed from a polymeric gel or foam.

There is also disclosed a stabilized cannula assembly including a cannula assembly having a valve body and an elongate tubular member extending distally from the valve body. The stabilized cannula assembly further includes a stabilizing member positionable upon the elongate tubular member such that the stabilizing member is swellable from an initial dimension to a greater final dimension in response to the absorption of a liquid. In one embodiment, the stabilizing member is fixedly secured to the elongate tubular member of the cannula assembly.

In an alternative embodiment, the stabilizing member it is movably mounted relative to the elongate tubular member of the cannula assembly such that the stabilizing member may be moved longitudinally relative to the elongate tubular member. In this embodiment, the stabilizing member is mounted on a hollow tube movably mounted on the elongate tubular member. In a particular embodiment, the hollow tube includes a locking member to secure the hollow tube longitudinally relative to the elongate tubular member.

DESCRIPTION OF THE DRAWINGS

Various embodiments of the presently disclosed stabilization assist device are disclosed herein with reference to the drawings, wherein:

FIG. 5 is a perspective view of an incision in tissue;

FIG. 6A is a side view, shown in section, of the stabilization assist device of FIG. 1 inserted through the incision in the tissue;

FIG. 6B is a side view, shown in section, similar to FIG. 6A with the stabilization assist device in the expanded or swelled condition;

FIG. 7 is a perspective view of another embodiment of a stabilization assist device movably mounted on a cannula shaft;

DETAILED DESCRIPTION OF EMBODIMENTS

Embodiments of the presently disclosed stabilization assist device or "stabilizer" will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
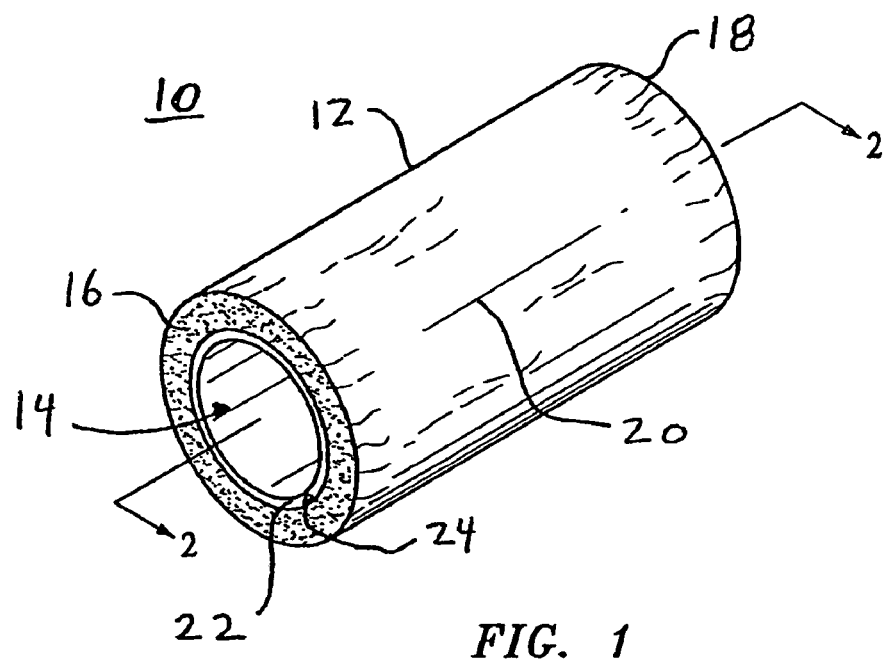
FIG. 1 is a perspective view of one embodiment of a stabilization assist device.

Referring to FIG. 1, there is disclosed a novel stabilization assist device or stabilizer 10 for use with a cannula type access port during endoscopic or laparoscopic surgeries. Stabilizer 10 is provided to secure the cannula through an abdominal wall to control the depth of the cannula through the abdominal wall as well as preventing any substantial flexing or pivoting relative to the abdominal wall. While stabilizer 10 is disclosed herein for use with a cannula in endoscopic or laparoscopic surgery, it should be noted that stabilizer 10 may find application in various other surgical situations, such as, for example, stabilizing a needle during intravenous surgery, stabilizing a tube during endotracheal applications, etc.

Stabilizer 10 generally includes a tube or collar 12 which is configured to be positioned about the tube of a cannula assembly. Collar 12 is formed of a hydrophilic polymer coating material or swellable polymeric gel or foam material which expands in size in response to the absorption of a liquid. By positioning collar 12 on a tube of a cannula assembly, collar 12 can swell in size to fill the opening of an incision in tissue and thereby secure the cannula assembly within the tissue incision. Collar 12 may be formed of different materials which may include, but are not limited to, sodium acrylate (NaA) and potassium sulfopropyl acrylate (KSPA), poly(2-hydroxyethyl methacrylate), poly(ethylene glycol), poly(lactic acid), poly(glycolic acid), polyurethanes, poly(caprolactone), poly(methyl methacrylate) polyacrylamides, polyacrylates, poly(methacrylic acid), poly(sulfonic acid), poly(styrene)poly(propylene oxide)polysaccharides such as alginate, chitosan, carboxymethylcellulose (CMC), dehydrated vegetable cellulose, and copolymers/blends thereof.

Additionally, the swellable material forming collar 12 may be reversible to reduce the size of collar 12 by displacement of the liquid out of collar 12. This may be accomplished by introducing a salt solution into collar 12 or by other methods which draw or force the liquid out of collar 12. In this manner the size of collar 12 may be reduced to facilitate removal of collar 12, and thus of the associated cannula, out of an incision in a patient.

Collar 12 defines a bore 14 extending from a distal end 16 to a proximal end 18 of collar 12 for receipt of the tube of a cannula assembly. In order to facilitate positioning collar 12 about the tube of a cannula assembly, collar 12 may be provided with a longitudinal slit 20 so that collar 12 may be wrapped about the tube of the cannula assembly. Collar 12 may be also provided with an adhesive layer 22 in order to secure a collar 12 to the tube of the cannula assembly. Adhesive layer 22 is formed on an inner surface 24 of collar 12 and may consist of any suitable adhesive type coating or material.

Figure 2:
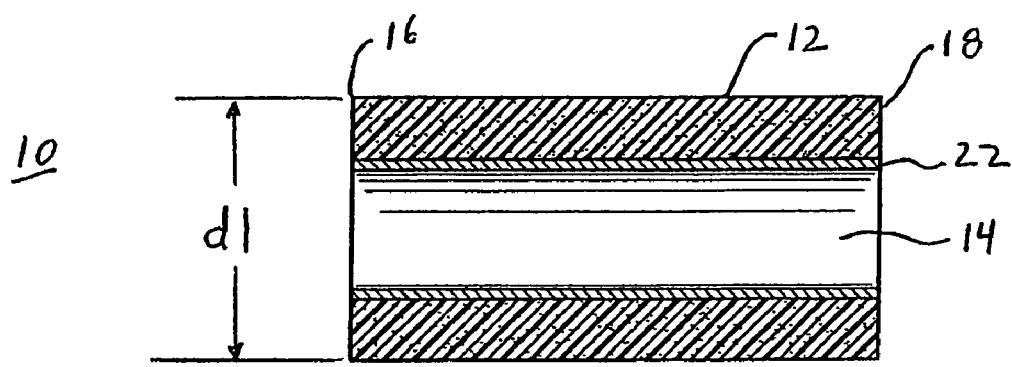
FIG. 2 is a side view, shown in section, taken along the line 2-2 of FIG. 1.
Figure 3:
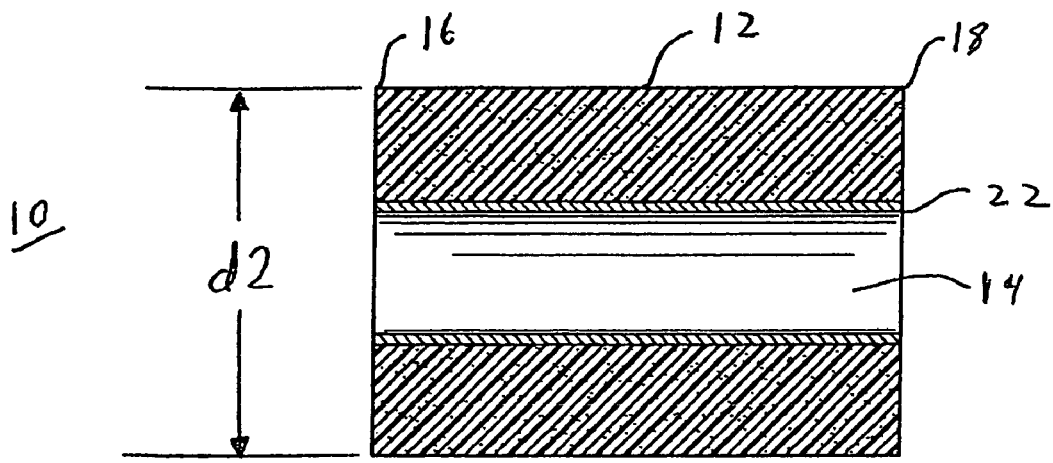
FIG. 3 is a side view, shown in section, similar to FIG. 2 with the stabilization assist device in an expanded or swelled condition.

Referring now to FIGS. 2 and 3, and initially with regard to FIG. 2, it can be seen that in the initial or unexpanded condition, collar 12 has a predetermined initial outer diameter of d1. Predetermined outer diameter d1 is sized to facilitate insertion of collar 12 and the associated cannula tube through an incision through tissue. Referring now to FIG. 3, collar 12 is formed such that it expands to a predetermined maximum outer diameter d2 in response to the absorption of a liquid. The liquid absorbed by collar 12 may include bodily fluids absorbed through the edges of the incision in the patient or may be provided by a separate external source such as, for example, a syringe, etc.

Figure 4:
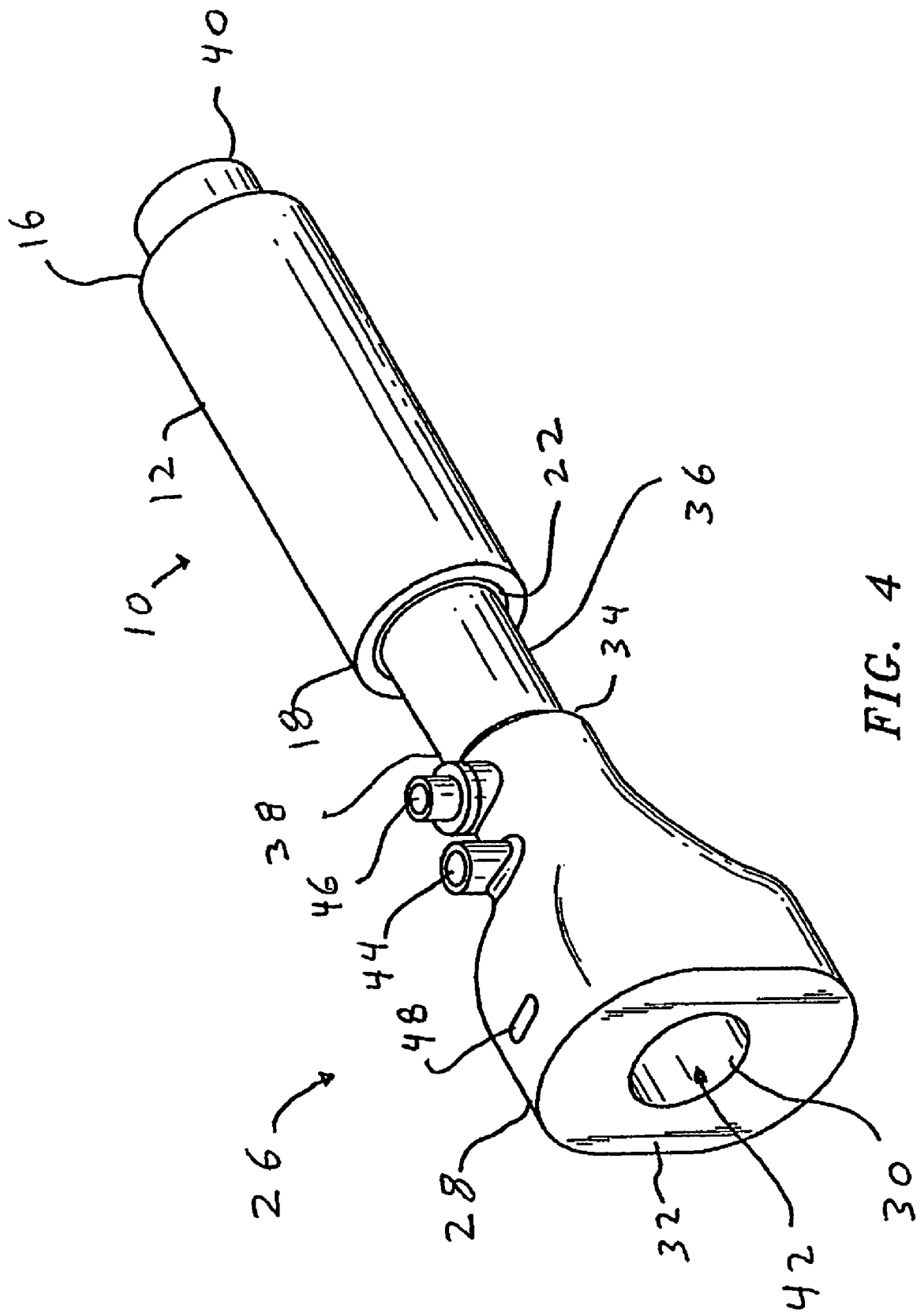
FIG. 4 is perspective view of the stabilization assist device of FIG. 1 mounted on a cannula.

Referring to FIG. 4, and is noted hereinabove, stabilizer 10 is configured for use with a cannula assembly of the type typically used in laparoscopic or endoscopic surgeries, such as, cannula assembly 26. Cannula assembly 26 generally includes a valve housing or body 28 having an opening 30 in a proximal end 32. Opening 30 extends from proximal end 32 to a distal end 34 of body 28. An elongate tubular member 36 extends distally from body 28 such that a proximal end 38 of elongate tubular member 36 extends from distal end 34 of body 28. Elongate tubular member 36 terminates in a distal end 40 such that a throughbore 42 is defined from opening 30 at proximal end 32 of body 28 to distal end 40 of elongate tubular member 36. Throughbore 42 is sized and dimensioned for receipt of various surgical instruments used during typical laparoscopic and endoscopic surgeries.

Cannula assembly 26 may further include one or more ports 44, 46 in body 28 for use in injecting and exhausting various insufflation fluids gases and/or dyes into and out of the body of a patient. Additionally, body 28 may include one or more notches 48 for engagement with various auxiliary instrumentation, such as, for example, tissue penetrating trocars, optical instrumentation, etc.

Referring now to FIGS. 5, 6A and 6B, and initially with regard to FIG. 5, the use of stabilizer 10 to support cannula assembly 26 within the tissue of a patient will now be described. In a typical endoscopic and/or laparoscopic surgery an initial incision I is made through a tissue T, such as, for example, an abdominal wall. Referring now to FIG. 6A, elongate tubular member 36, having stabilizer 10 mounted thereon, is inserted through incision I such that the appropriate depth of elongate tubular member 36 within the abdominal cavity is achieved. As noted hereinabove, stabilizer 12 has an initial predetermined outer dimension d1 which is small enough to be easily inserted through incision I. Referring now to FIG. 6B, once elongate tubular member 36 has probably been positioned within incision I, collar 12 swells towards the maximum outer diameter d2 in response to the absorption of bodily fluids from tissue T. Additionally, and or alternatively, a syringe may be used to inject liquids into collar 12 such that collar 12 absorbs the liquids and expands towards its maximum outer diameter d2.

As collar 12 expands towards its maximum outer diameter d2, a central portion 50 of collar 12 swells to a diameter d3 to fill incision I. Central portion 50 fills the entire area of incision I and may assume various asymmetric shapes corresponding to the edges of incision I. A distal portion 52 of collar 12 swells to its maximum outer diameter d3 such that an edge 54 is formed between distal portion 52 and central portion 50. Similarly, a proximal portion 56 expands to maximum outer diameter d2 and forms an edge 58 between proximal portion 56 and central portion 50. Edges 54 and 58 prevent longitudinal movement of cannula assembly 26 through tissue T to stabilize cannula assembly 26 longitudinally relative to tissue T. Edges 54 and 58 further cooperate to provide stabilizing surfaces against tissue T to aid in preventing cannula assembly 26 from flexing or rocking relative to tissue T.

Thereafter, various endoscopic or laparoscopic surgical procedures may be performed through cannula assembly 26. Once the various surgeries have been completed, and as noted hereinabove, various solutions, such as, for example, a salt solution may be applied to collar 12 to draw liquids out of collar 12 and cause collar 12 to shrink back to its initial diameter d1. Thereafter, cannula assembly 26, having stabilizer 10 thereon, may be removed from the incision and the surgery completed.

Referring now to FIGS. 7, 8 and 9, and initially with regard to FIG. 7, there is disclosed an alternative embodiment of a stabilization device or stabilizer 60 for use with a cannula assembly. Stabilizer 60 is configured to be longitudinally adjustable along the length of elongate tubular member 36 of cannula assembly 26. Stabilizer 60 generally includes an elongate tubular member 62 having a distal end 64 and a proximal end 66. A throughbore 68 extends from proximal end 66 to distal end 64 for receipt of elongate tubular member 36 of cannula assembly 26. A clamp assembly 70 is provided at proximal end 66 of elongate tubular member 62 and allows elongate tubular member 62 to be fixedly secured at a desired position along the length of elongate tubular member 36. Clamp assembly 70 generally includes a locking member in the form of a spring biased collar 72 which defines an adjustable opening 74. Opening 74 allows adjustable stabilizer 60 to be longitudinally moved along elongate tubular member 36 when opening 74 is in the open most position and secures adjustable stabilizer 60 along the length of elongate tubular member 36 when opening 74 is moved to the closed position. A pair of wings 76 and 78 are provided on collar 72 to move collar 72 between the opened and closed positions.

Adjustable stabilizer 60 further includes swellable collar 12 having adhesive layer 22 which fixedly secures collar 12 about elongate tubular member 62 in a manner substantially identical to that described hereinabove with regard to stabilizer 10.

Figure 8A:
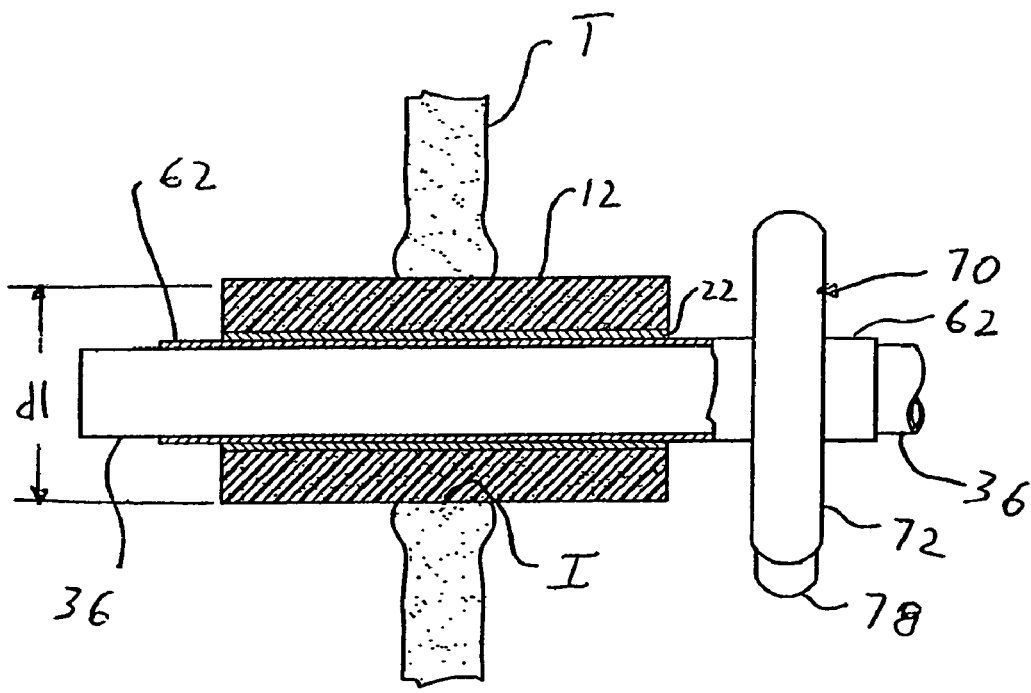
FIG. 8A is a side view, shown in section, of the stabilization assist device of FIG. 7 inserted through an incision in tissue.
Figure 8B:
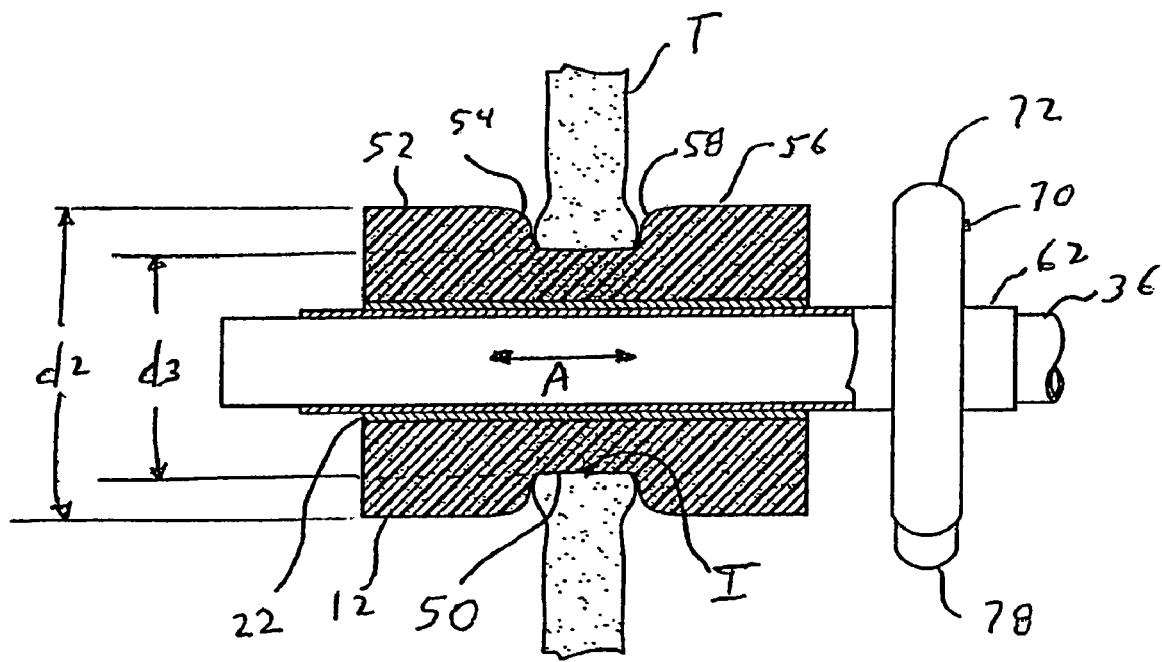
FIG. 8B is a side view, shown in section, similar to FIG. 8A with the stabilization assist device in the expanded or swelled condition.

Referring now to FIG. 8A, similar to that described hereinabove with regard to stabilizer 10, in use, elongate tubular member 36 having stabilizer 60 mounted thereon is inserted through incision I such that the appropriate depth of elongate tubular member 36 within the abdominal cavity is achieved. Collar 12 has predetermined outer dimension d1 which is small enough to be easily inserted through incision I. Referring now to FIG. 8B, once elongate tubular member 36 has probably been positioned within incision I, collar 12 swells towards the maximum outer diameter d2 in response to the absorption of bodily fluids from tissue T. As discussed hereinabove, a syringe may be used to inject liquids into collar 12 such that collar 12 absorbs the liquids and expands towards its maximum outer diameter d2.

As collar 12 expands towards its maximum outer diameter d2, central portion 50 of collar 12 swells to diameter d3 to fill incision I. Central portion 50 fills the entire area of incision I and may assume various asymmetric shapes corresponding to the edges of incision I. Distal portion 52 of collar 12 swells to its maximum outer diameter d3 as does proximal portion 56. Similar to that described hereinabove with regard to stabilizer 10, edges 54 and 58 prevent longitudinal movement of elongate tubular member 62 of adjustable stabilizer 60 relative to tissue T. Edges 54 and 58 also cooperate to provide stabilizing surfaces against tissue T to aid in preventing stabilizer 60, and thus cannula assembly 26, from flexing or rocking relative to tissue T.

Once collar 12 has swelled to secure adjustable stabilizer 60 relative to tissue T, clamp assembly 70 including collar 72 may be opened by compressing wings 76 and 78 to release collar 72 from elongate tubular member 36 of cannula assembly 26. Thereafter, cannula assembly 26 is free to move longitudinally through adjustable stabilizer 62 in the directions of arrow A so as to adjust cannula assembly 26, and specifically, elongate tubular member 36, to the proper depth within the abdominal cavity. Once elongate tubular member 36 has been properly positioned within the abdominal cavity, wings 76, 78 may be released to compress collar 72 about elongate tubular member 36 thereby securing cannula assembly 26 longitudinally relative to adjustable stabilizer 60 and tissue T.

Similar to that described hereinabove, various endoscopic or laparoscopic surgical procedures may now be performed through cannula assembly 26. Once the operation has been completed, and as noted hereinabove, various solutions, such as, for example, a salt solution may be applied to collar 12 to draw liquids out of collar 12 and cause collar 12 to shrink back to its initial diameter d1. Thereafter, cannula assembly 26, having stabilizer 10 thereon, may be removed from the incision and the surgery completed. Thus, adjustable stabilizer 60 provides a novel method of securing cannula assembly 26 at a desired depth within, and against the longitudinal movement relative to, incision I in tissue T and prevents cannula assembly 26 from flexing or falling over at an angle relative to tissue T.

It will be understood that various modifications may be made to the embodiments disclosed herein. For example, collar 12 need not be formed as a cylindrical member but may take other configurations such as oval, square, etc. sufficient to fill an incision formed in tissue. Further, other methods, such as the provision of powders, or other hydrophilic substances, may be provided to draw out fluids from the disclosed stabilizer so as to reduce the dimension of the stabilizer from an expanded to an initial position for removal of the stabilizer. Additionally, as noted hereinabove, the disclosed stabilizer may find use in other surgical applications, such as, for example, intravenous procedures, endotracheal procedures, or other procedures requiring stabilization of a member relative to surrounding tissue. Therefore, the above description should not be construed as limiting, but merely as exemplifications of particular embodiments. Those skilled in the art will envision other modifications within the scope and spirit of the claims appended hereto.

The invention claimed is:
1. A stabilized cannula assembly comprising:
    a cannula assembly having a valve body, and an elongate tubular member extending distally from the valve body configured and dimensioned for positioning within an opening in tissue; and a stabilizing member positionable upon the elongate tubular member, the stabilizing member including a proximal portion, a central portion and a distal portion, and configured and dimensioned such that at least a section of the distal portion extends beneath tissue, the stabilizing member reconfigurable between first and second configurations in response to the absorption of a liquid, the stabilizing member defining a first transverse cross-sectional configuration in the first configuration, and a second, larger transverse cross-sectional configuration in the second configuration, whereby the stabilizing member abuts adjacent tissue portions defining the opening such that the stabilizing member defines a first edge positioned proximally of the tissue, and a second edge positioned distally of the tissue, the first and second edges substantially inhibiting longitudinal movement of the stabilizing member within the opening in the tissue;

wherein the stabilizing member is movably mounted relative to the elongate tubular member of the cannula assembly such that the stabilizing member may be moved longitudinally relative to the elongate tubular member;

wherein the stabilizing member is mounted on a hollow tube movably mounted on the elongate tubular member; and wherein the hollow tube includes a locking member to secure the hollow tube longitudinally relative to the elongate tubular member.

* * * * *